US007112174B2

(12) United States Patent
Satoh et al.

(10) Patent No.: US 7,112,174 B2
(45) Date of Patent: Sep. 26, 2006

(54) PULSE WAVE DETECTION DEVICE AND METHOD OF DETECTING PULSE WAVE, WHEREIN PULSE WAVE IS DETECTED WITH SELECTION OF PRESSURE SENSOR FOR PULSE WAVE DETECTION FROM PLURALITY OF PRESSURE SENSORS

(75) Inventors: Hironori Satoh, Moriyama (JP); Takashi Inagaki, Kameoka (JP); Ryo Fukui, Kadoma (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/137,368

(22) Filed: May 26, 2005

(65) Prior Publication Data

US 2005/0267375 A1    Dec. 1, 2005

(30) Foreign Application Priority Data

May 31, 2004   (JP)   ............................. 2004-161633

(51) Int. Cl.
*A61B 5/02*   (2006.01)

(52) U.S. Cl. ................ 600/500; 600/501; 600/503

(58) Field of Classification Search ................ 600/481, 600/485, 490–503
See application file for complete search history.

(56) References Cited

U.S. PATENT DOCUMENTS 4,409,983 A   10/1983   Albert 6,447,456 B1 *   9/2002   Tsubata ...................... 600/455
6,953,435 B1 *   10/2005   Kondo et al. ............... 600/485
2002/0095092 A1 *   7/2002   Kondo et al. ............... 600/503

FOREIGN PATENT DOCUMENTS

| EP | 0778001 A  | 6/1997 |
| FR | 2700684 A  | 7/1994 |
| JP | 06-114018  | 4/1994 |

OTHER PUBLICATIONS

European Search Report mailed Sep. 21, 2005 directed to corresponding EP Application No. 05011379.4.

\* cited by examiner

*Primary Examiner*—Robert L. Nasser
*Assistant Examiner*—Navin Natnithithadha
(74) *Attorney, Agent, or Firm*—Morrison & Foerster LLP

(57) ABSTRACT

A sensor array having a plurality of pressure sensors arranged on a measurement surface, a pressurization portion for pressing the sensor array laid across an artery of a living body, a sensor signal selection portion for selecting a pressure signal among pressure signals from the plurality of pressure sensors, a filter portion having a cutoff frequency variable corresponding to an instruction, and a filter control portion for providing an instruction to vary a value of the cutoff frequency are included. The filter control portion switches the cutoff frequency in a situation wherein a plurality of pressure signals respectively obtained from the plurality of pressure sensors are successively switched and output by the sensor signal selection portion to specify the pressure sensor for pulse wave detection, and in a situation wherein the pulse wave is detected from the specified pressure sensor.

10 Claims, 12 Drawing Sheets

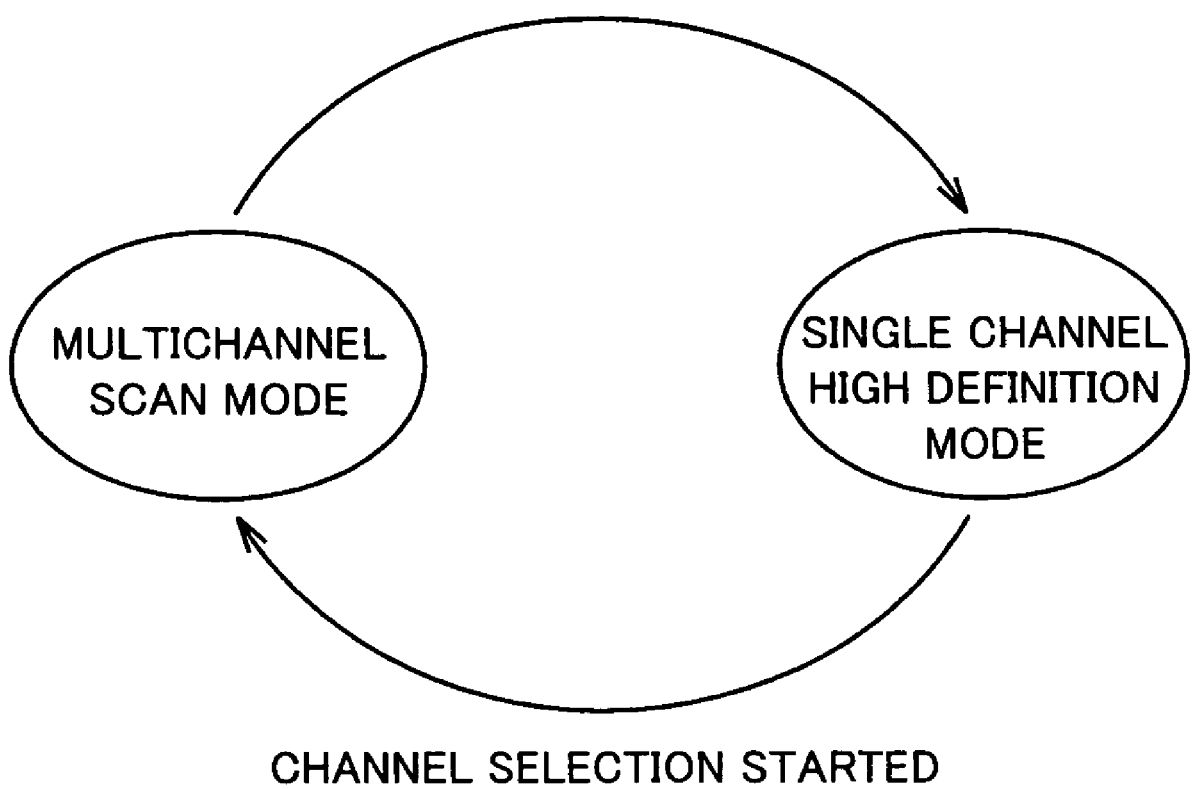

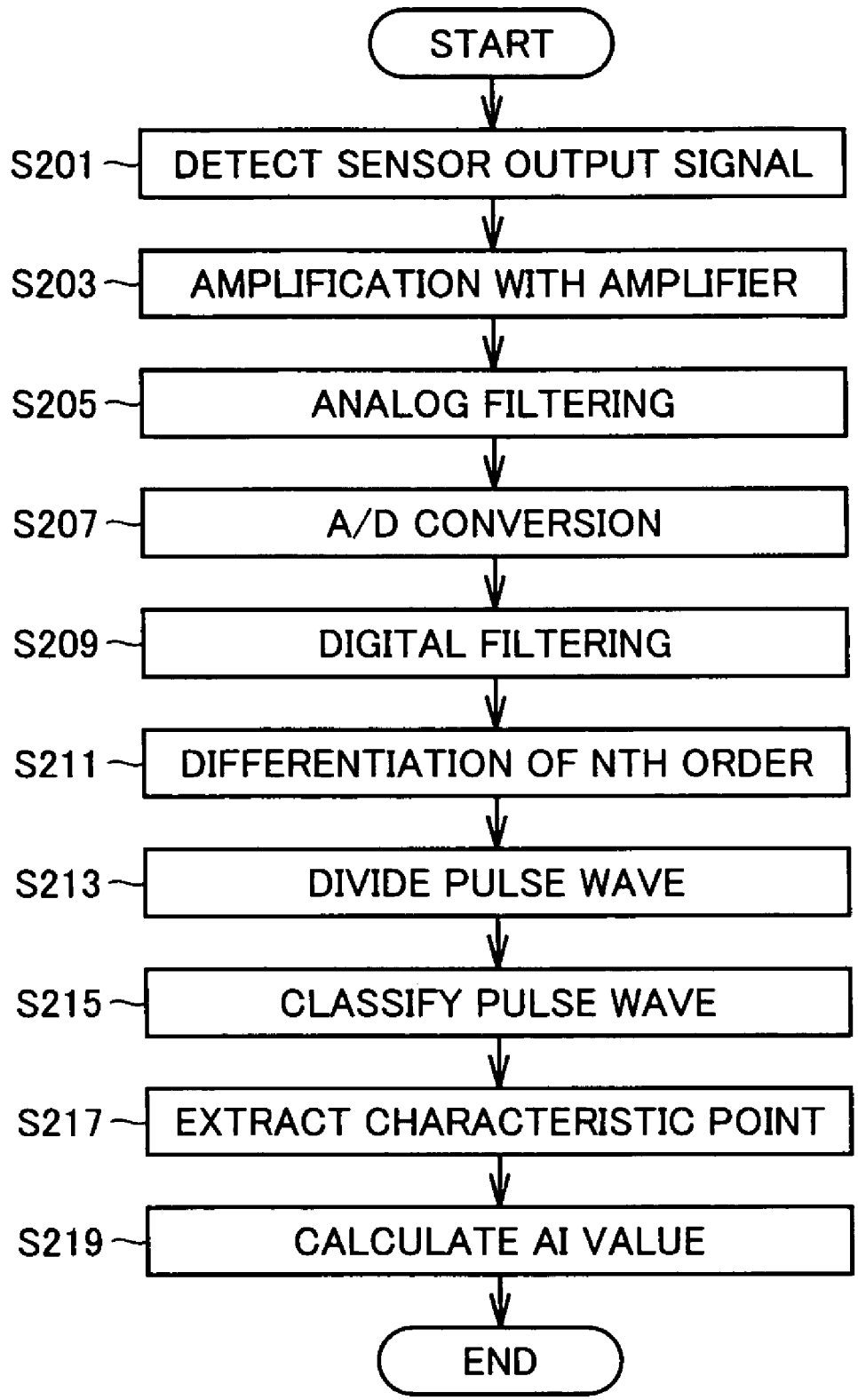

PULSE WAVE DETECTION DEVICE AND METHOD OF DETECTING PULSE WAVE, WHEREIN PULSE WAVE IS DETECTED WITH SELECTION OF PRESSURE SENSOR FOR PULSE WAVE DETECTION FROM PLURALITY OF PRESSURE SENSORS

BACKGROUND OF THE INVENTION

1. Field of the Invention

The present invention relates to a pulse wave detection device and a method of detecting a pulse wave. More specifically, the present invention relates to a pulse wave detection device and a method of detecting a pulse wave wherein a pulse wave is detected with selection of a pressure sensor for pulse wave detection from a plurality of pressure sensors.

2. Description of the Invention

A pulse wave is detected based on pressure information which is a voltage signal obtained from a pressure sensor pressed against a surface over an artery of a living body. For accurate detection of the pulse wave, a plurality of pressure sensors are utilized and the pulse wave is measured based on the pressure information from an optimum pressure sensor which is located above a central portion of an artery.

A pressure pulse wave detection device is conventionally known which uses a multiplexer to multiplex pressure information obtained from a plurality of pressure sensors into a signal line for detection (see Japanese Patent Laying-Open No. 06-114018). With a multiplexer as such, a number of lines between pressure sensors and A/D (Analog/Digital) converters as well as a number of A/D converters can be decreased.

In a conventional pulse wave detection device, however, since pressure information is obtained with switching among the plurality of pressure sensors using the multiplexer to select an optimum sensor, a noise cannot be sufficiently eliminated to ascertain a characteristic of a waveform when the pulse wave is to be measured after selection of the optimum sensor.

SUMMARY OF THE INVENTION

The present invention is made to solve the problem as described above. An object of the present invention is to provide a pulse wave detection device and a method of detecting a pulse wave each allowing accurate detection of a pulse wave.

A pulse wave detection device according to one aspect of the present invention includes a sensor array having a plurality of pressure sensors arranged on a measurement surface, a pressurization portion for pressing the sensor array laid across an artery of a living body, a sensor signal selection portion for selecting a pressure signal among pressure signals from the plurality of pressure sensors, a filter portion having a cutoff frequency variable corresponding to an instruction, an analog/digital conversion portion for converting an analog signal passed through and output from the filter portion into a digital signal, a pressure sensor specification portion for specifying a pressure sensor for pulse wave detection among the plurality of pressure sensors, a pulse wave detection portion for detecting a pulse wave from the artery based on the digital signal corresponding to the pressure signal from the pressure sensor specified by the pressure sensor specification portion, and a filter control portion for providing the instruction to vary the cutoff frequency in the filter portion.

The above-described filter portion cuts off a signal component having a frequency of at least a prescribed value included in the pressure signal selected by the sensor signal selection portion corresponding to the cutoff frequency.

The filter control portion switches the cutoff frequency from a first value in a first situation wherein a plurality of pressure signals respectively obtained from the plurality of pressure sensors are successively switched and output by the sensor signal selection portion to specify the pressure sensor for pulse wave detection, to a second value in a second situation wherein the pulse wave is detected by the pulse wave detection portion.

Preferably, the first value corresponds to a value of at least a switching frequency of the plurality of pressure signals in the first situation, and the second value corresponds to a value enabling to eliminate an aliasing noise in the second situation.

The value enabling to eliminate the aliasing noise is preferably at most half a value of a sampling frequency for one pressure signal of the plurality of pressure signals.

The filter portion preferably includes a plurality of filters having different frequency characteristics, and an output selection portion for selecting one output among outputs from the plurality of filters.

The above-described plurality of filters include a first filter having the cutoff frequency of a value of at least a switching frequency of the plurality of pressure signals and a second filter having the cutoff frequency of a value enabling to eliminate an aliasing noise, and the filter control portion makes the output selection portion select an output from the first filter in the first situation and an output from the second filter in the second situation.

In addition, the filter portion preferably includes a variable capacitance element having a capacitance varying corresponding to a voltage applied from the outside, and the filter control portion varies the value of the cutoff frequency by applying a voltage to the variable capacitance element.

The above-described pulse wave detection device preferably further includes a sensor signal selection control portion for controlling an operation of the sensor signal selection portion. The sensor signal selection control portion switches between a first operation to successively switch and output the plurality of pressure signals respectively obtained from the plurality of pressure sensors and a second operation to select and output the pressure signal from the specified pressure sensor.

The filter control portion preferably provides an instruction to set the value of the cutoff frequency in the filter portion to a value of at least a switching frequency of the plurality of pressure signals during selection of the pressure sensor for pulse wave detection, and to a value enabling to eliminate an aliasing noise when a pulse wave is detected based on the pressure signal output from the specified pressure sensor.

Preferably, adjustment of a pressurization level of the pressurization portion and selection of the pressure sensor for pulse wave detection are performed concurrently.

According to another aspect of the present invention, a method of detecting a pulse wave includes the steps of selecting a pressure signal with successively switching a plurality of pressure signals respectively obtained from a plurality of pressure sensors arranged on a measurement surface, low-pass-filtering the selected pressure signal with a first cutoff frequency, specifying a pressure sensor for pulse wave detection among the plurality of pressure sensors based on the low-pass-filtered pressure signal, selecting a pressure signal from the pressure sensor specified among the plurality of pressure signals as a pulse wave signal for pulse wave detection, low-pass-filtering the selected pulse wave signal with a second cutoff frequency lower than the first cutoff frequency, and detecting a pulse wave from the low-pass-filtered pulse wave signal.

Preferably, the first cutoff frequency has a value of at least a switching frequency of the plurality of pressure signals, and the second cutoff frequency has a value of at most half a value of a sampling frequency for one pressure signal of the plurality of pressure signals.

According to the present invention, a noise can be decreased by providing the filter portion having a variable value of the cutoff frequency. In addition, decreased noise can increase accuracy of a pulse wave analysis for each pulse.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 shows an example of mode transition of the characteristic variable filter of the pulse wave detection device in the first embodiment of the present invention.

FIG. 9 shows sensor signal analysis processing in the first embodiment of the present invention.

DESCRIPTION OF THE PREFERRED EMBODIMENT

Figure 1:
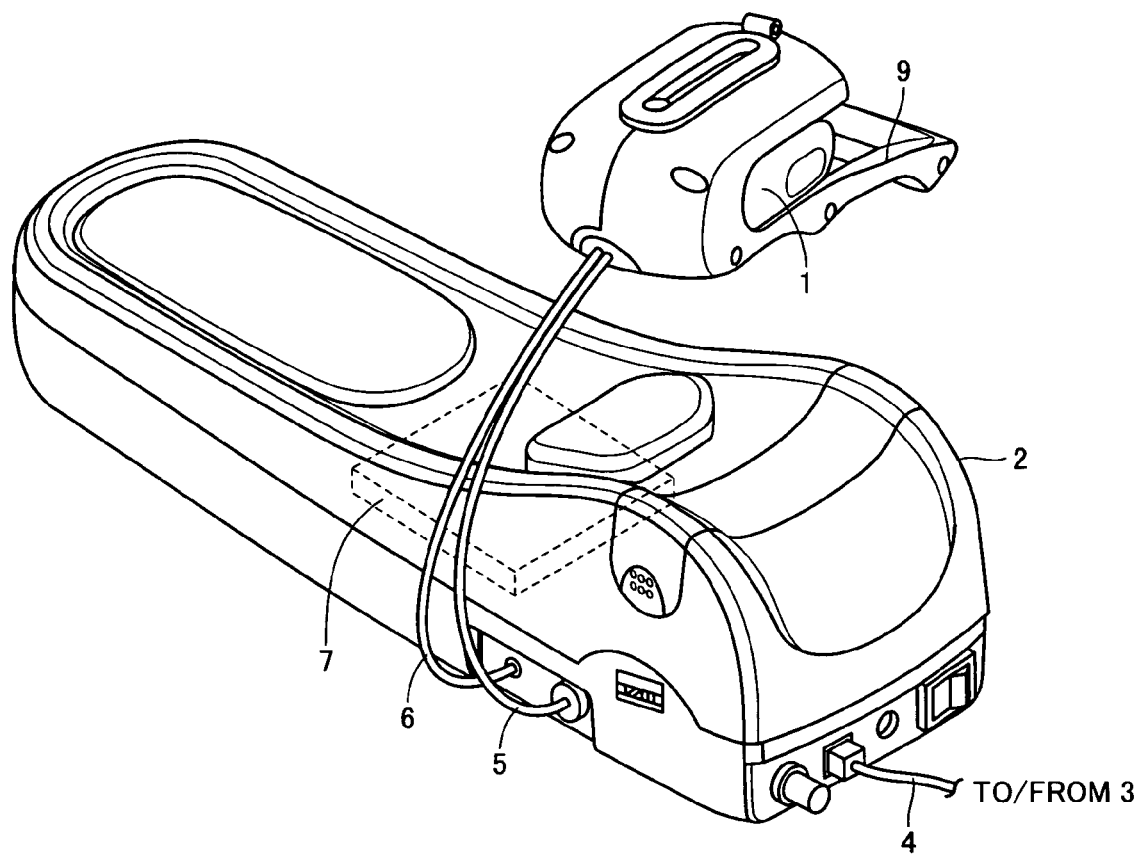
FIG. 1 shows a way of connection between a sensor unit and a fixing base in a first embodiment of the present invention.

An embodiment of the present invention will now be described in detail referring to the drawings. The same or corresponding portions are indicated with the same characters in the drawings and descriptions thereof will not be repeated.

First Embodiment

Figure 2:
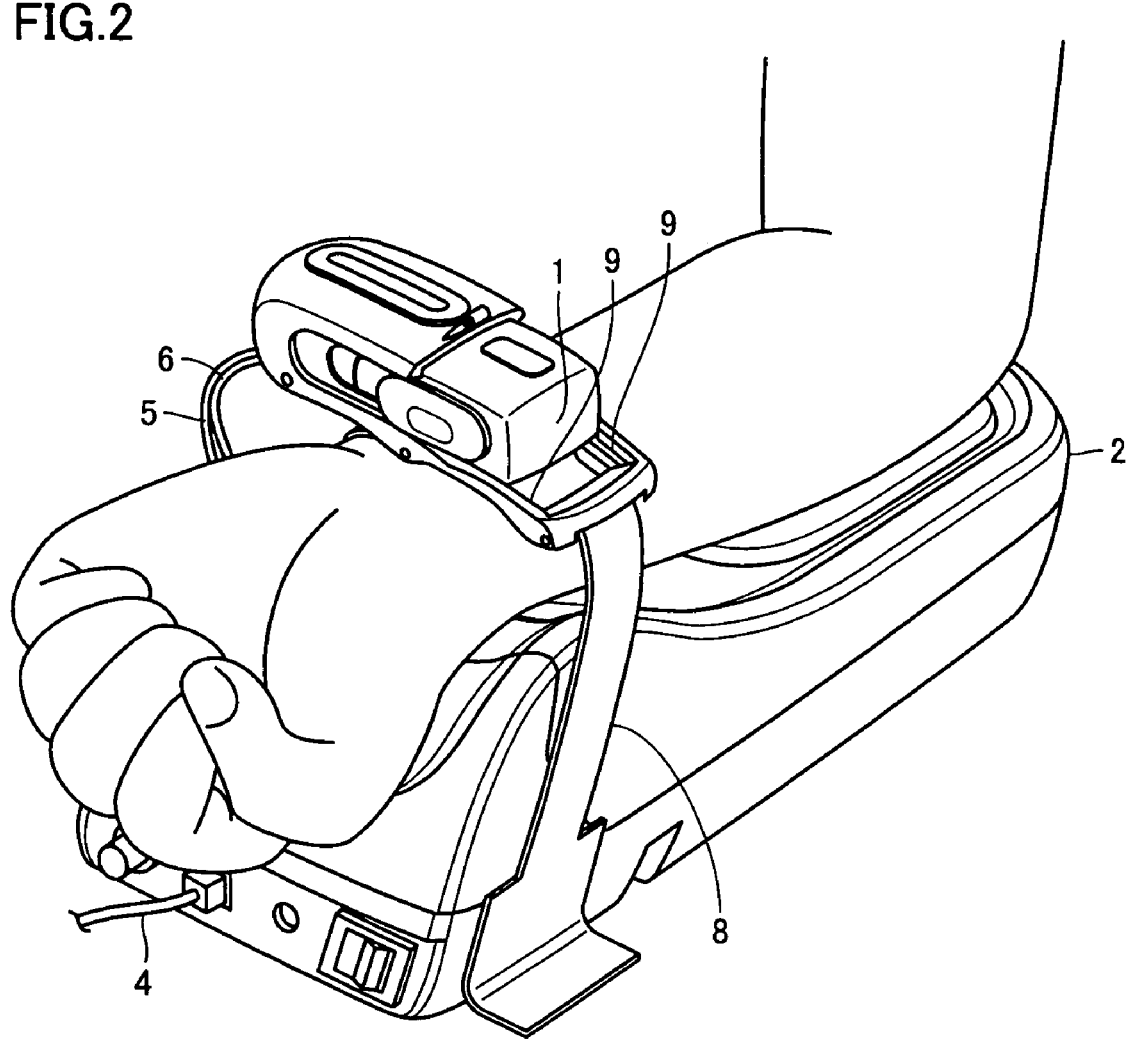
FIG. 2 shows a way of using for pulse wave measurement in the first embodiment of the present invention.

Exterior and Construction of Pulse Wave Detection Device in First Embodiment of the Present Invention FIG. 1 shows a connection between a sensor unit and a fixing base. FIG. 2 shows a state of a pulse wave detection device mounted on a living body.

Referring to FIGS. 1 and 2, the pulse wave detection device includes a sensor unit 1 which is mounted on a surface of a wrist to detect a pulse wave in an artery of the wrist, a fixing base 2 for fixing the wrist for pulse wave detection, and a display unit 3 (not shown) for inputting and outputting various information regarding the pulse wave detection. In FIG. 1, sensor unit 1 is located inside a housing. In FIG. 2, sensor unit 1 is slid via a slide groove 9 (see FIG. 1) to move outside the housing and is located on the wrist.

Fixing base 2 has a fixing base unit 7 provided therein. Fixing base unit 7 and display unit 3 are connected via a USB (Universal Serial Bus) cable 4 to allow communication therebetween. In addition, fixing base unit 7 and sensor unit 1 are connected via a communication cable 5 and an air tube 6.

As shown in FIG. 2, to detect a pulse wave, a user mounts a wrist on a prescribed position on fixing base 2, slides sensor unit 1 to locate it on a surface of an artery side of the wrist, and fastens the housing of sensor unit 1 and fixing base 2 with a belt 8 to immobilize sensor unit 1 on the wrist.

Figure 3:
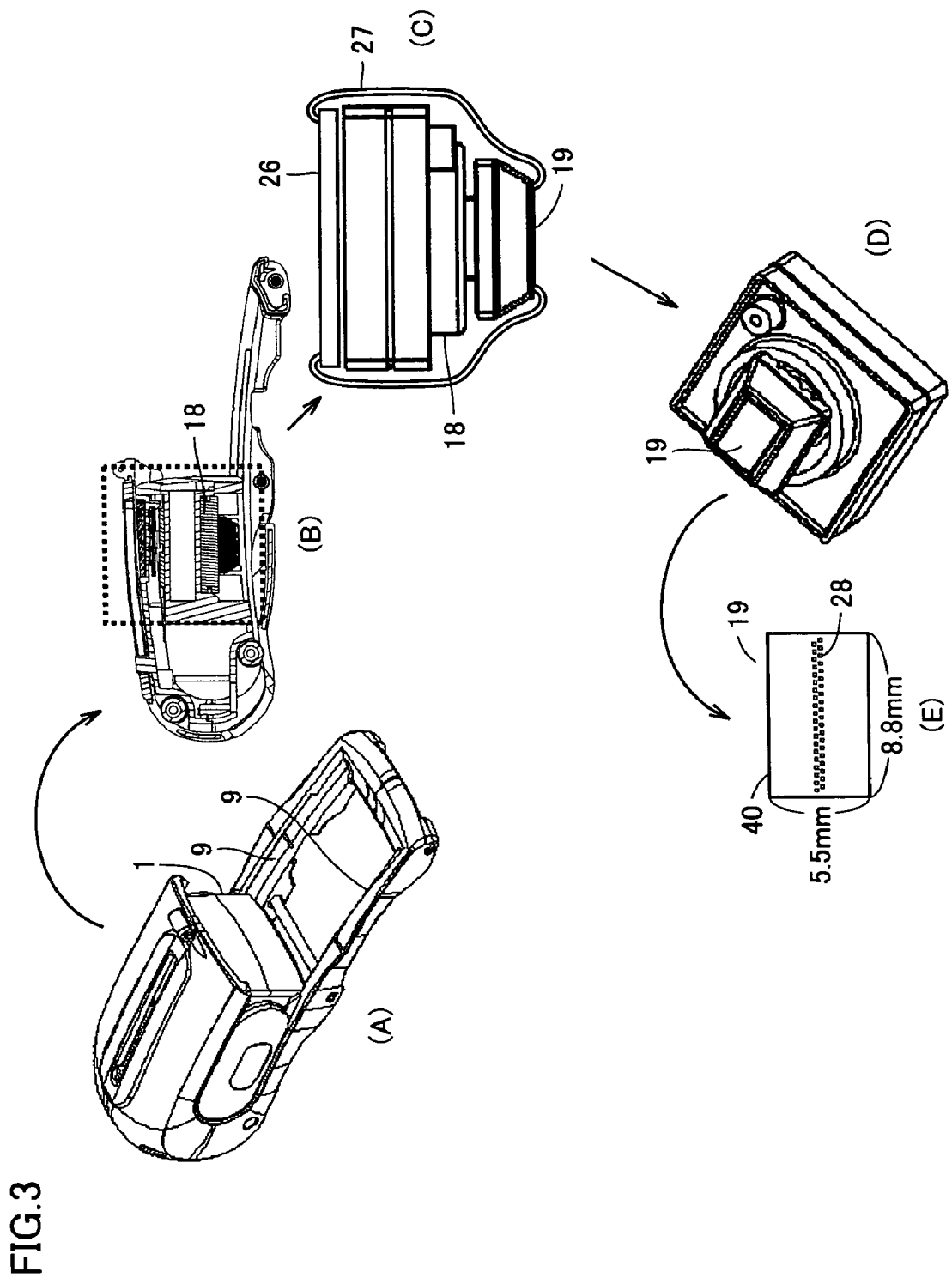
FIG. 3 shows a construction of the sensor unit in the first embodiment of the present invention.

FIG. 3 shows a construction of sensor unit 1.

In FIG. 3, (B) shows a cross-sectional structure of sensor unit 1 shown in (A), which is cut in a direction across the wrist on which the sensor unit is mounted. A portion inside a box indicated with broken lines in (B) is enlarged and shown in (C) of FIG. 3. A cuff pressure of a pressurization cuff 18 shown in (B) of FIG. 3 is adjusted with a booster pump 15 and a suction pump 16, and a semiconductor pressure sensor 19 attached via a block molded with ceramic or resin freely moves upward or downward with an amount corresponding to a level of the cuff pressure. Semiconductor pressure sensor 19 is moved downward to project from an opening previously provided in the housing, and is pressed against a surface of the wrist.

As shown in (D) and (E) of FIG. 3, an arrangement of a plurality of sensor elements 28 in semiconductor pressure sensor 19 extends in a direction corresponding to a substantially perpendicular (crossing) direction to an artery when sensor unit 1 is mounted on the wrist, and has a length longer than a diameter of the artery. When pressed with a cuff pressure of pressurization cuff 18, each of sensor elements 28 outputs pressure information, which is a pressure oscillation wave generated from the artery and transmitted to a surface of a living body, as a voltage signal (hereafter referred to as a "pressure signal"). In this embodiment, 40 sensor elements 28, for example, are arranged on a measurement surface 40 having a prescribed dimension (5.5 mm×8.8 mm).

Referring to (C) of FIG. 3, the pressure signal from sensor element 28 is sent via a flexible wiring 27 to a multiplexer 20 and an amplifier 21 in a PCB (Printed Circuit Board) 26, successively.

Figure 4:
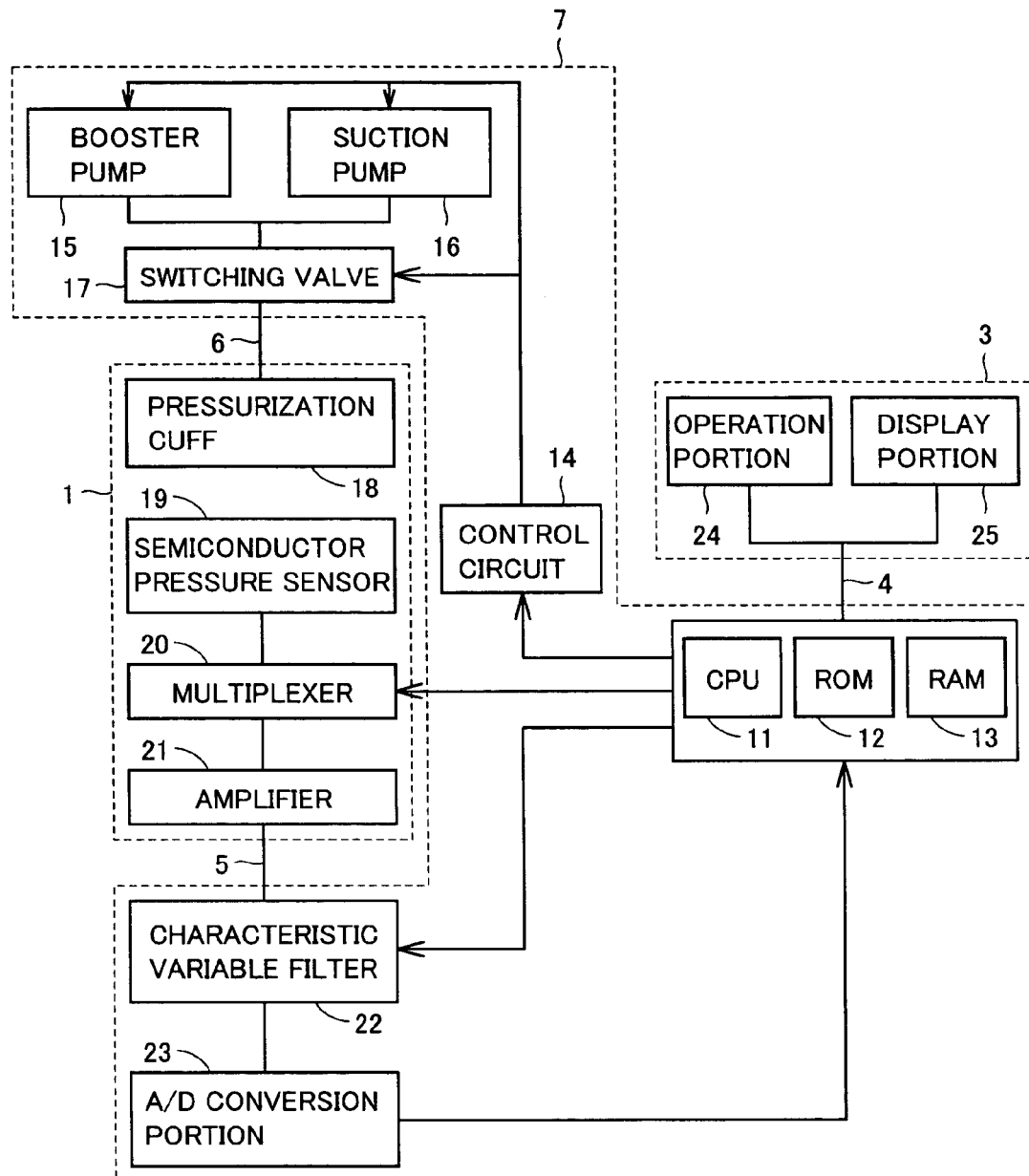
FIG. 4 shows a functional construction of a pulse wave detection device in the first embodiment of the present invention.

FIG. 4 shows a functional construction of the pulse wave detection device in the first embodiment of the present invention. Referring to FIG. 4, display unit 3 includes an operation portion 24 provided to allow operation from the outside and operated to input various information regarding pulse wave detection, and a display portion 25 formed with an LED (Light Emitting Diode), an LCD (Liquid Crystal Display) or the like for outputting various information such as results of artery position detection and pulse wave measurement to the outside.

Fixing base unit 7 includes an ROM (Read Only Memory) 12 and an RAM (Random Access Memory) 13 for storing data or a program to control the pulse wave detection device, a CPU (Central Processing Unit) 11 for performing various processing including an operation for concentrated control of the pulse wave detection device, booster pump 15, suction pump 16, a switching valve 17, a control circuit 14 for transmitting a signal received from CPU 11 to booster pump 15, suction pump 16 and switching valve 17, a characteristic variable filter 22 which can be varied to at least two values, and an A/D conversion portion 23.

CPU 11 accesses ROM 12 to read a program and expands the program on RAM 13 for execution to control the whole pulse wave detection device. CPU 11 receives from operation portion 24 an operation signal from a user and performs control processing of the whole pulse wave detection device based on the operation signal. That is, CPU 11 sends a control signal based on the operation signal input from operation portion 24. CPU 11 also displays a result of pulse wave detection and the like on display portion 25.

Booster pump 15 is a pump for boosting an internal pressure (hereafter referred to as a "cuff pressure") of pressurization cuff (an air bag) 18 described below, and suction pump 16 is a pump for decreasing the cuff pressure. Switching valve 17 selectively switches one of booster pump 15 and suction pump 16 and connects to air tube 6. Control circuit 14 controls these elements.

Sensor unit 1 includes semiconductor pressure sensor 19 including a plurality of sensor elements 28, multiplexer 20 selectively deriving a pressure signal output from each of the plurality of sensor elements, amplifier 21 for amplifying the pressure signal output from multiplexer 20, and pressurization cuff 18 including the air bag having a pressure adjusted to press semiconductor pressure sensor 19 against a wrist.

Semiconductor pressure sensor 19 is formed with a semiconductor chip made of single crystal silicon or the like including a plurality of sensor elements arranged in one direction with a prescribed spacing (see (E) of FIG. 3), and is pressed against a measurement region such as a wrist of a measured subject with a pressure of pressurization cuff 18. In this state, semiconductor pressure sensor 19 detects a pulse wave of the subject via a radial artery. Semiconductor pressure sensor 19 inputs the pressure signal output with detection of the pulse wave to multiplexer 20 for each channel of sensor element 28.

Multiplexer 20 selectively outputs the pressure signal output from each sensor element 28. The pressure signal sent from multiplexer 20 is amplified in amplifier 21 and selectively output to A/D conversion portion 23 via characteristic variable filter 22. In this embodiment, multiplexer 20 is dynamically controlled by CPU 11.

Characteristic variable filter 22 is a low pass filter having a variable cutoff frequency to cut off a signal component of at least a prescribed value. Characteristic variable filter 22 will be described below in detail.

A/D conversion portion 23 converts the pressure signal, which is an analog signal derived from semiconductor pressure sensor 19, into digital information and provides the result to CPU 11. CPU 11 concurrently obtains the pressure signal output from each sensor element 28 included in semiconductor pressure sensor 19 along a time axis via multiplexer 20.

Since CPU 11, ROM 12 and RAM 13 are included in fixing base unit 7 in this embodiment, display unit 3 can be made smaller.

It is to be noted that, though fixing base unit 7 of fixing base 2 and display unit 3 are separately provided, fixing base 2 may include both functions. In addition, though CPU 11, ROM 12 and RAM 13 are included in fixing base unit 7, they may be included in display unit 3. Furthermore, a PC (Personal Computer) may be connected to perform various control.

Sensor Selection Processing in Pulse Wave
Detection Device (Without Characteristic Variable
Filter)

Though characteristic variable filter 22 is provided in the pulse wave detection device in the first embodiment of the present invention, an operation is possible without characteristic variable filter 22.

As a precondition for describing an operation and a construction of the pulse wave detection device shown in FIG. 4, an operation without presence of characteristic variable filter 22 will be described in the following.

The pulse wave detection device first uses multiplexer 20 to select an optimum sensor element 28 for pulse wave detection among the plurality of sensor elements 28. When the optimum sensor element 28 is specified, a pulse wave is detected with a pressure signal obtained from that specified sensor element 28.

Figure 12:
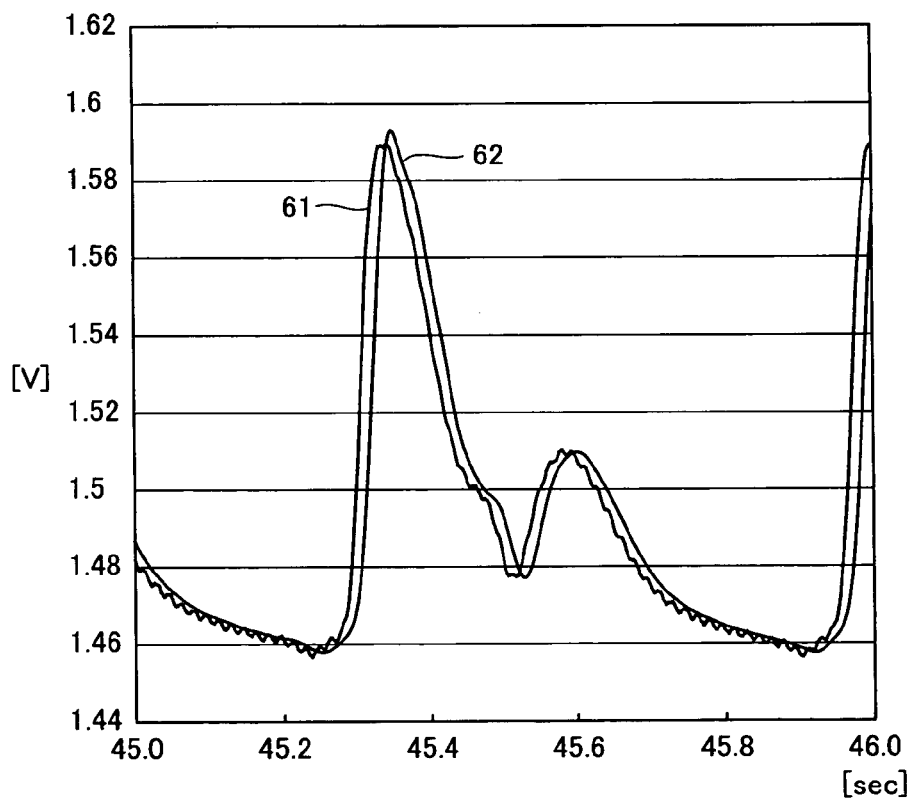
FIG. 12 is a diagram for describing a problem with a pulse wave detection device in which an antialiasing filter is not applied.

Waveform data 61 shown in FIG. 12 is pulse wave data corresponding to an arbitrary one pulse just after A/D conversion, which is obtained based on the pressure signal obtained from one channel in the pulse wave detection device without application of characteristic variable filter 22. In this waveform data 61, a noise having a small amplitude is seen in a portion having a small variation in a voltage (for example, near 45.0–45.2 seconds and near 45.8 seconds).

Figure 13A:
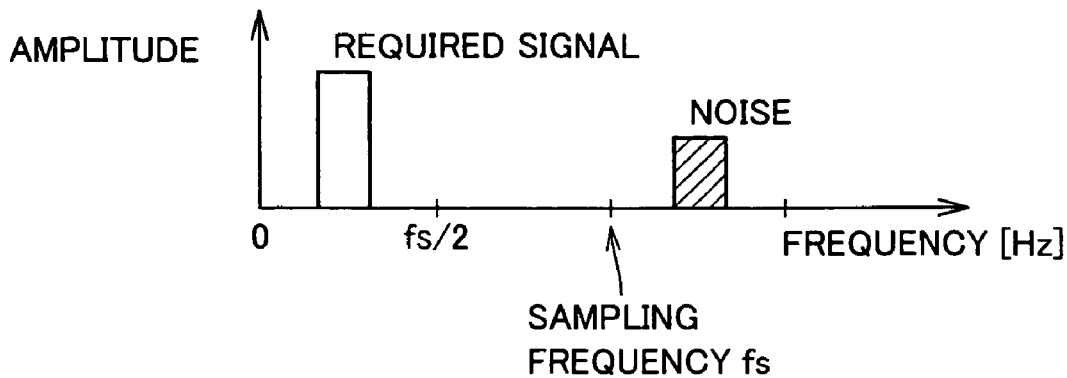
FIG. 13A is a first diagram for describing an aliasing noise.
Figure 13B:
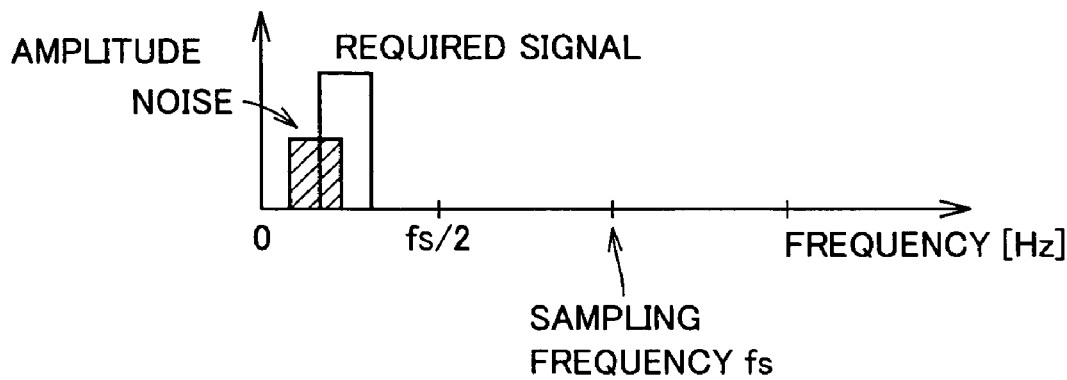
FIG. 13B is a second diagram for describing an aliasing noise.

The noise appearing in waveform data 61 in FIG. 12 may be an aliasing noise. Referring to FIGS. 13A and 13B, the aliasing noise is a noise having a frequency component of at least half a value of a sampling frequency (see FIG. 13A), which undesirably appears in a region of at most half a value of the sampling frequency by aliasing (see FIG. 13B) when an analog signal is converted into a digital signal according to a sampling theorem. Therefore, the aliasing noise cannot be eliminated by digital filtering after A/D conversion because the aliasing noise is included in a required signal.

Pulse wave analysis may fail due to a minute noise especially because differentiation and the like are performed. Therefore, high accuracy must be ensured in pulse wave detection and, for this purpose, it is very important to eliminate the noise.

Figure 14:
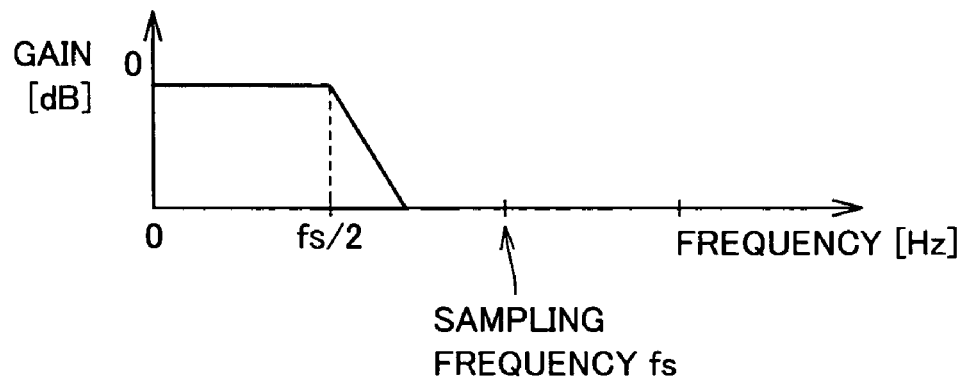
FIG. 14 shows a frequency characteristic of a low pass filter required to eliminate the aliasing noise.

Thus, as shown in FIG. 14, a low pass filter (hereafter referred to as an "antialiasing filter") may be inserted before the A/D conversion to cut off a signal component of at least half a value of a sampling frequency fs.

Figure 15A:
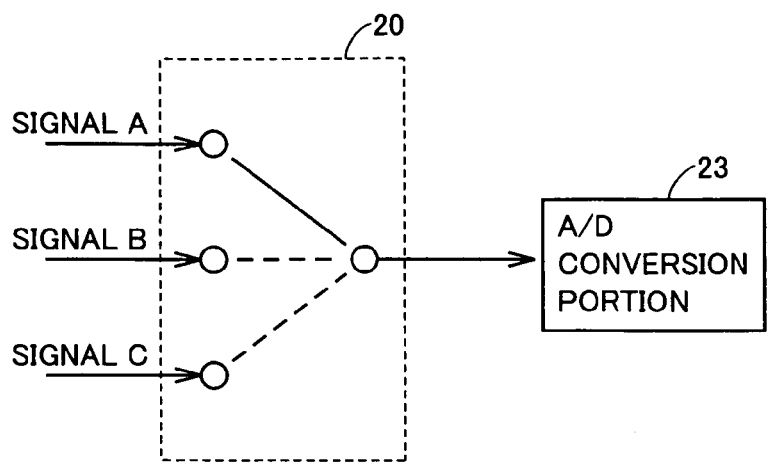
FIG. 15A is a first diagram for describing a switching frequency of a multiplexer.
Figure 15B:
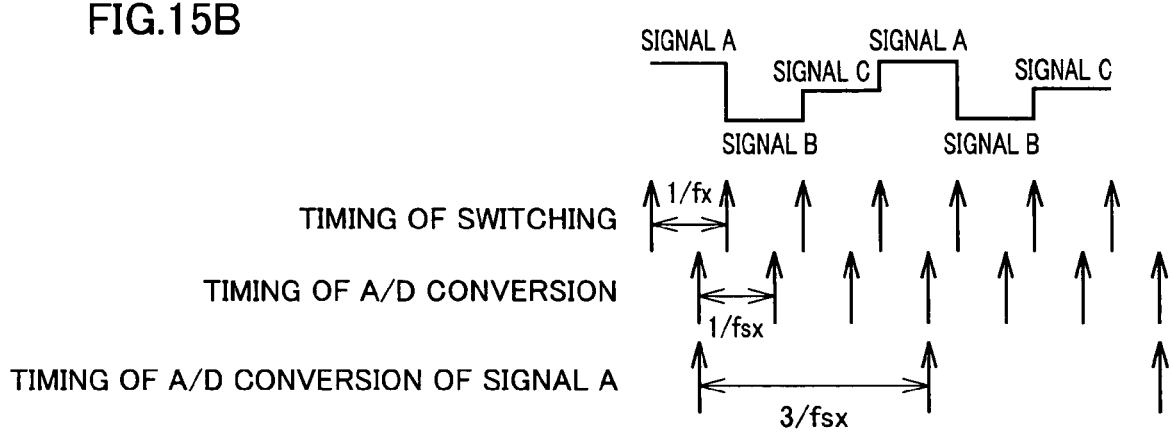
FIG. 15B is a second diagram for describing a switching frequency of a multiplexer.

Referring to FIG. 15A, when multiplexer 20 transfers pressure signals A, B and C to one A/D conversion portion 23 with time division, for example, and when switching by multiplexer 20 and A/D conversion in A/D conversion portion 23 are performed with the same clock, a switching frequency fx of a plurality of pressure signals A, B and C is equal to a switching sampling frequency fsx which is a sampling frequency at a time of switching, as shown in FIG. 15B.

When signal A is noted in this situation, a sampling frequency fsa of signal A becomes fsa=fsx/3. Therefore, an appropriate cutoff frequency fca of an antialiasing filter required for signal A becomes fca=fsa/2, that is, fca=fsx/6.

When the antialiasing filter as such is applied, a waveform should be ideally a smooth curve as waveform data 62.

Figure 16:
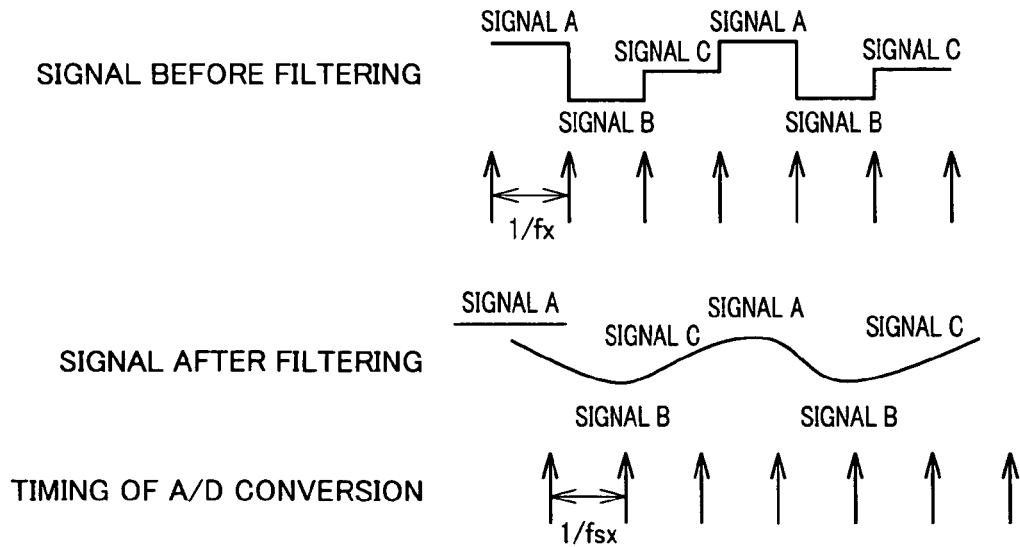
FIG. 16 is a diagram for describing a problem with application of the antialiasing filter during an operation of the multiplexer.

Referring to FIG. 16, however, when an analog filter having cutoff frequency fca=fsx/6 is applied while a plurality of signals are switched with multiplexer 20, rounding occurs because a frequency component of at least fsx/6 is cut off. This makes reconstitution of an original waveform difficult, and thus the optimum sensor element 28 cannot be selected. Therefore, since sampling is performed with switching among signals A, B and C using multiplexer 20 until the optimum sensor element 28 is selected, the antialiasing filter as such cannot be simply inserted.

As described above, an antialiasing filter cannot be fixedly applied to the pulse wave detection device which selects sensor element 28 for pulse wave detection with switching among a plurality of pressure signals using multiplexer 20. Therefore, in the pulse wave detection device which does not include characteristic variable filter 22, the noise shown in waveform data 61 in FIG. 12 cannot be eliminated, which makes it difficult to perform a pulse wave analysis with high accuracy.

<Operation and Construction of Pulse Wave Detection Device in First Embodiment of the Present Invention>

An operation of the pulse wave detection device having characteristic variable filter 22 in the first embodiment of the present invention will now be described.

Figure 5:
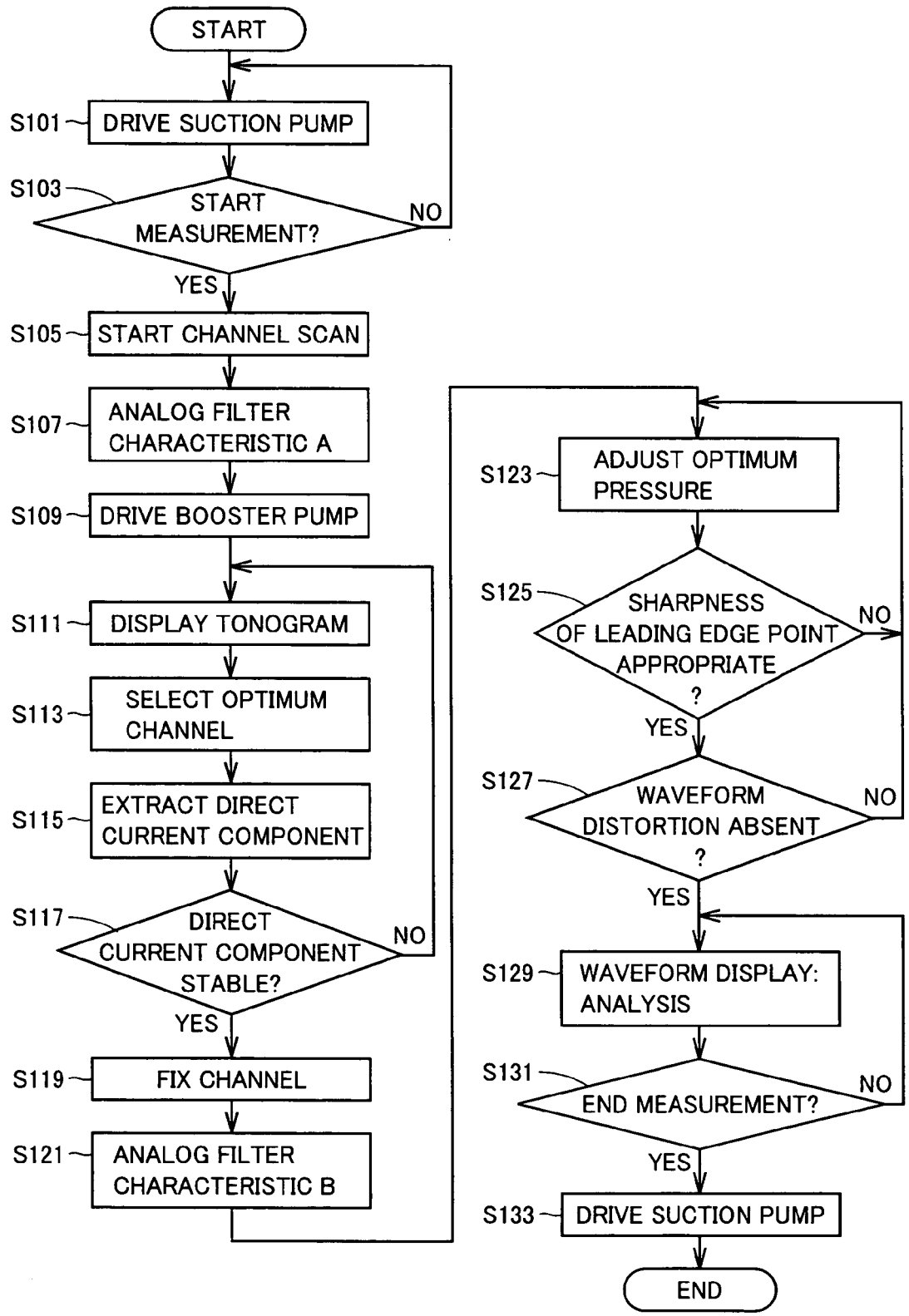
FIG. 5 is a flow chart of pulse wave measurement processing in the first embodiment of the present invention.

FIG. 5 is a flow chart of pulse wave measurement processing in the first embodiment. Processing shown in the flow chart of FIG. 5 is performed by CPU 11 which accesses ROM 12 to read a program and expands the program on RAM 13 for execution.

Referring to FIG. 5, when a power supply switch (not shown) is turned on, CPU 11 provides an instruction to control circuit 14 to drive suction pump 16, and control circuit 14 switches switching valve 17 to a side of suction pump 16 based on this instruction and drives suction pump 16 (S101). By driving of suction pump 16, the cuff pressure is made sufficiently lower than an atmospheric pressure via switching valve 17, and therefore accidental projection of a sensor portion including semiconductor pressure sensor 19, which causes a malfunction or a failure, can be avoided.

Thereafter, movement of the sensor portion to a measurement region, pressing of a measurement start switch (not shown) included in operation portion 24 or the like is sensed and a determination is made to start measurement (S103). In the former situation, the sensor portion includes a microswitch or the like, which is not shown, for sensing the movement thereof, and CPU 11 determines as to whether the sensor portion has moved or not based on a detection signal of the microswitch.

Figure 6:
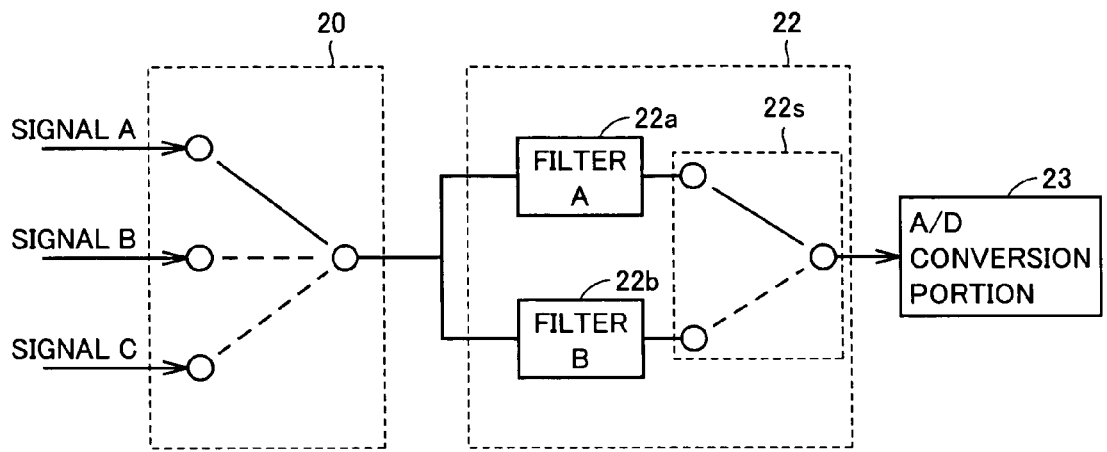
FIG. 6 is a diagram for describing a filter switching circuit forming a characteristic variable filter in the first embodiment of the present invention.

When a start of the measurement is determined (YES in S103), CPU 11 operates multiplexer 20 and starts a channel scan to obtain a pressure signal from each sensor element 28 (S105). In this situation, CPU 11 sets a characteristic of a cutoff frequency of characteristic variable filter 22 to a characteristic A. As shown in FIG. 6, in the first embodiment, a control signal is transmitted to an output selection portion 22s of a switching circuit forming characteristic variable filter 22 to select a filter A 22a (S107). As a result, output selection portion 22s selects an output signal from filter A 22a and provides the signal to A/D conversion portion 23.

Then, CPU 11 sends a control signal to control circuit 14 to drive booster pump 15. Based on this control signal, control circuit 14 switches switching valve 17 to a side of booster pump 15 and drives booster pump 15 (S109). With this, the cuff pressure is increased and the sensor portion including semiconductor pressure sensor 19 is pressed against a surface of a measurement region of a subject.

When the sensor portion is pressed against the measurement region, the pressure signal from each sensor element 28 included in semiconductor pressure sensor 19 is subject to time division with multiplexer 20 and amplified with amplifier 21. An amplified pressure signal is then input to filter A 22a. The pressure signal filtered with filter A 22a is sent to A/D conversion portion 23. The signal is then converted into digital information in A/D conversion portion 23 and input to CPU 11. CPU 11 makes a tonogram using the digital information and displays the result on display portion 25 (S111).

Next, CPU 11 detects sensor element 28 located above the artery based on the tonogram made in S111, and executes processing for selecting that sensor element 28 as an optimum channel (S113). It is to be noted that, a technique such as that described in Japanese Patent Laying-Open No. 2004-222847 (U.S. Pub. No. US2004/0193061A1), which was filed by the same applicant as the present application and was laid open, can be used as the processing for selecting an optimum channel.

In this embodiment, it is assumed that one sensor element 28 is adopted as the optimum channel.

At the same time, CPU 11 extracts a direct current component from the pressure signal input from each sensor element 28 (S115). The direct current component can be derived from an average value of the pressure signal in a constant time, or a component of the pressure signal which passed through the low pass filter (a component after removal of a pulse wave), or a pressure signal level at a leading edge point of a pulse wave (just before mixing of a pulse wave component).

More specifically, in step S115, the direct current component can be extracted by dividing an output variation of the pressure signal into windows (sections) each corresponding to a constant time, and calculating an average in each window. Alternatively, the direct current component can be similarly extracted by, for example, calculating a median value of a maximum value and a minimum value in each window, or extracting a value of at most a prescribed frequency using a low pass filter. It is to be noted that, the constant time described above is a time interval previously set in the pulse wave detection device which is independent of a pulse of a subject, and is preferably about 1.5 seconds which includes a general time for one pulse.

Then, CPU 11 detects from the pressure signal input from each sensor element 28 a site at which the direct current component extracted in step S115 is stable (S117). When the site with the stable direct current component is not detected (NO in S117), processing of steps S111–S117 described above is repeated with continued boosting for pressurization cuff 18 by booster pump 15 until the site with the stable direct current component is detected.

As described above, by concurrently performing processing for selection of the optimum channel and processing for adjustment of an optimum pressure by detection of the direct current component, a time required before a start of pulse wave measurement can be decreased.

It is to be noted that, the optimum pressure may be adjusted after the optimum channel is selected.

When the selection of the optimum channel is completed and the site with the stable direct current component is detected (YES in S117), CPU 11 fixes the channel so that the pressure signal from sensor element 28 determined as the optimum channel is selected and sent to multiplexer 20 (S119). At the same time, CPU 11 switches the characteristic of the cutoff frequency of characteristic variable filter 22 to a characteristic B (S121). In the first embodiment, a control signal for switching to a filter B 22b shown in FIG. 6 is transmitted to output selection portion 22s of the switching circuit of characteristic variable filter 22. As a result, output selection portion 22s selects an output from filter B 22b and provides to A/D conversion portion 23.

Then, a pressurization force corresponding to the site with the stable direct current component detected in S117 is determined as an optimum pressurization force of pressurization cuff 18, and a control signal is sent to control circuit 14 to adjust a pressure of pressurization cuff 18 (S123).

After the pressurization force of pressurization cuff 18 is determined as the optimum pressurization force in step S123, CPU 11 determines as to whether sharpness of a leading edge point of waveform data, that is, the pressure signal output from sensor element 28 selected as the optimum channel while pressurization cuff 18 is kept with the optimum pressurization force, is appropriate or not (S125), and as to whether there is a waveform distortion or not (S127).

When the sharpness of the leading edge point of the waveform data is inappropriate (NO in S125), or when the waveform distortion is detected (NO in S127), adjustment of the pressurization force in step S123 is repeated until the sharpness of the leading edge point of the waveform data becomes appropriate or until the waveform distortion is not detected.

When the sharpness of the leading edge point of the waveform data is appropriate (YES in S125) and the waveform distortion is not detected (YES in S127), CPU 11 obtains the waveform data at that time point via multiplexer 20, amplifier 21, filter B 22b and A/D conversion portion 23 (S129).

In this situation, since the channel is fixed in S119, multiplexer 20 sends only the pressure signal from a single channel to filter B 22b via amplifier 21. The pressure signal filtered with filter B 22b is then converted into a digital signal in A/D conversion portion 23.

Then, CPU 11 detects a pulse wave from the obtained waveform data, and determines as to whether a prescribed condition for ending pulse wave detection is met or not (S131). The condition for ending pulse wave detection in S131 may be a lapse of a prescribed time previously set (for example, 30 seconds), or may be an instruction from a user for ending (or discontinuance). That is, transferring of pulse wave data in step S129 described above is repeated until the prescribed condition is met.

When the prescribed condition for ending pulse wave detection is met (YES in S131), CPU 11 sends a control signal to control circuit 14 to drive suction pump 16 via switching valve 17 (S133). With this, a pressed state of the sensor portion against the measurement region is released, and a series of pulse wave measurement processing is ended.

As described above, in the first embodiment, CPU 11 controls multiplexer 20 with switching between an operation for a channel scan in S105 and an operation for fixing the channel in S119. In the pulse wave detection device in this embodiment, the channel can be fixed as such because there is a low possibility of deviation of the channel due to movement of a body during pulse wave measurement, since a time for pulse wave measurement is as short as about 30 seconds to 2 minutes.

Next, characteristic variable filter 22 in the embodiment of the present invention will be described using FIGS. 6–8.

Figure 7A:
FIG. 7A shows a frequency characteristic of a filter A.
Figure 7B:
FIG. 7B shows a frequency characteristic of a filter B.

FIG. 6 is a diagram for describing a filter switching circuit forming characteristic variable filter 22 in the first embodiment. Referring to FIG. 6, characteristic variable filter 22 includes filter A 22a, filter B 22b having a frequency characteristic different from filter A 22a, and output selection portion 22s for selecting one of outputs from these filters. Output selection portion 22s selects an output from one of filter A 22a and filter B 22b based on a signal provided from the outside. FIGS. 7A and 7B respectively show frequency characteristics of filter A 22a and filter B 22b shown in FIG. 6.

In this embodiment, as an example, it is assumed that switching frequency fx of pressure signals from 40 sensor elements 28 is 20 kHz. Then, sampling frequency fs of the pressure signal from one of the 40 sensor elements 28 becomes 500 Hz.

In the following description of the first embodiment, sampling frequency fs means a sampling frequency of a single pressure signal.

Referring to FIG. 7A, a cutoff frequency $fc_A$ of filter A 22a is set to 250 kHz, for example, a value not less than switching frequency fx (20 kHz). On the other hand, referring to FIG. 7B, a cutoff frequency $fc_B$ of filter B 22b is set to 100 Hz, for example, a value lower than half a value of sampling frequency fs, that is, fs/2 (250 Hz). In a condition as described above, cutoff frequency $fc_B$ of filter B 22b preferably satisfies 30 Hz<$fc_B$<250 Hz (=fs/2).

FIG. 8 shows an example of transition of characteristic variable filter 22 in the first embodiment.

Referring to FIG. 8, when selection of the optimum channel is started with successively switching the pressure signals from the plurality of sensor elements 28 with multiplexer 20, CPU 11 sets characteristic variable filter 22 to a multichannel scan mode. Then, after the selection of the optimum channel, the mode is changed to a single channel high definition mode. In the first embodiment, CPU 11 selects filter A 22a shown in FIG. 6 to set to the multichannel scan mode. In addition, CPU 11 switches to filter B 22b shown in FIG. 6 from filter A 22a to set to the single channel high definition mode.

As described above, filter A 22a is applied during the selection of the optimum channel since multiplexer 20 is operated to switch pressure signals. Since cutoff frequency $fc_A$ of filter A 22a is set to 250 kHz, which is sufficiently higher than switching frequency fx (20 kHz), lack of higher frequency information does not occur during reconstruction of a waveform.

Then, filter B 22b is applied after the selection of the optimum channel. Filter B 22b functioning as an antialiasing filter can be applied because CPU 11 controls multiplexer 20 to fix to a single channel after the selection of the optimum channel.

FIG. 9 is a flow chart of analysis processing of the pressure signal (a sensor signal) obtained from sensor element 28 in the pulse wave detection device of the first embodiment. The processing shown in the flow chart of FIG. 9 is also performed by CPU 11 in fixing base unit 7, which accesses ROM 12 to read a program and expands the program on RAM 13 for execution.

Referring to FIG. 9, when a pressure signal is detected in semiconductor pressure sensor 19 including a plurality of sensor elements 28 (S201), semiconductor pressure sensor 19 inputs the pressure signal to amplifier 21 via multiplexer 20. The pressure signal detected in semiconductor pressure sensor 19 is amplified with amplifier 21 to a prescribed frequency (S203), and passed through filter A 22a or filter B 22b forming characteristic variable filter 22 for analog filtering (S205).

Filter A 22a is applied by CPU 11 until the channel is fixed in S119 shown in FIG. 5, and filter B 22b is applied after the channel is fixed in S119.

The pressure signal passed through characteristic variable filter 22 is converted into a digital signal in A/D conversion portion 23 (S207), and subject to digital filtering for extracting a frequency in a prescribed range for a purpose of, for example, eliminating a noise (S209). Then, A/D conversion portion 23 transfers the pressure signal in a digital form to CPU 11.

Sensor signal analysis processing is ended here until the channel is fixed in S119 described above.

After the channel is fixed in S119, CPU 11 receives the pressure signal from A/D conversion portion 23 and executes the program stored in ROM 12 for differentiation of Nth order of a waveform of a pulse wave obtained from the pressure signal (S211). Then, the waveform of the pulse wave is divided based on a result of the differentiation to extract the waveform of the pulse wave for one pulse (S213), and the waveform of the pulse wave is classified (S215). Then, a prescribed characteristic point is extracted from the classified waveform of the pulse wave (S217), and an AI (Augmentation Index) value is calculated (S219). Thereafter, the sensor signal analysis processing is ended.

Figure 10A:
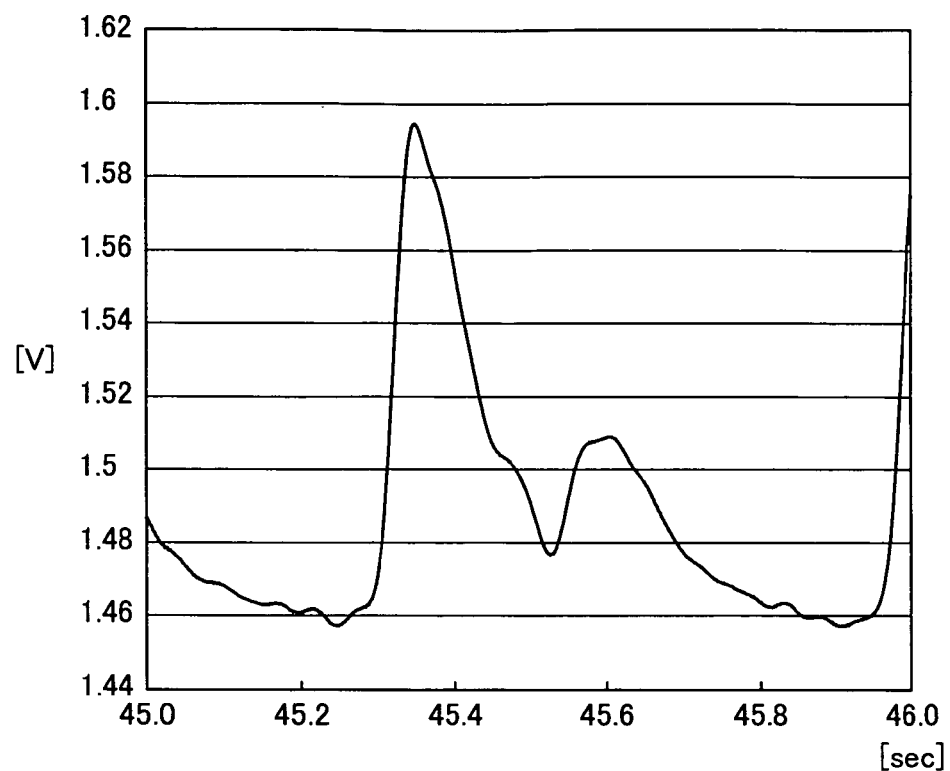
FIG. 10A shows an example of display of a pulse wave for one pulse when a frequency characteristic of the characteristic variable filter is set to a characteristic A.
Figure 10B:
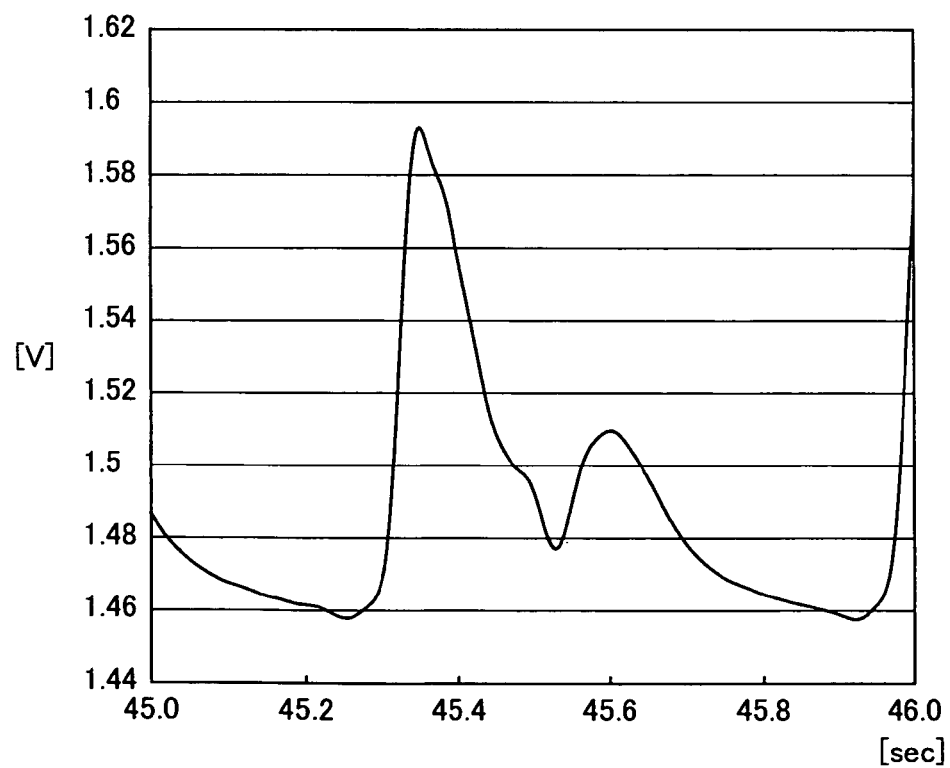
FIG. 10B shows an example of display of a pulse wave for one pulse when a frequency characteristic of the characteristic variable filter is set to a characteristic B.

FIG. 10A shows an example of display of the pulse wave for one pulse when the frequency characteristic of characteristic variable filter 22 is set to characteristic A in this embodiment. This situation is in the multichannel scan mode, and filter A 22a is applied. On the other hand, FIG. 10B shows an example of display of the pulse wave for one pulse when the frequency characteristic of characteristic variable filter 22 is set to characteristic B. This situation is in the single channel high definition mode, and filter B 22b is applied.

Referring to FIG. 10A, a small amplitude is seen in waveform data in a time period having a small variation in a voltage (for example, near 45.2 seconds and near 45.8 seconds), which shows that a noise is included. Referring to FIG. 10B, on the other hand, a smooth curve is shown even for the waveform data in the time period having a small variation in a voltage (for example, near 45.2 seconds and near 45.8 seconds), which shows that the noise is eliminated.

Therefore, since the waveform of the pulse wave for one pulse extracted in S213 of FIG. 9 is highly accurate, the AI value of high accuracy can be calculated in S219 from the waveform of the pulse wave for one pulse.

It is to be noted that, the aforementioned AI is a known index which indicates a characteristic amount reflecting intensity of reflection of a pulse wave (a reflection phenomenon of a pulse wave which represents acceptability of an outgoing blood flow) mainly corresponding to arteriosclerosis of a central blood vessel. AI is recognized as an effective index to find especially a circulatory disease at an early stage, and is known to behave differently from a blood pressure.

In this embodiment, an index such as $\Delta Tp$ may be calculated, which is known as a characteristic amount of a pulse wave.

Modified Example of Pulse Wave Detection Device in First Embodiment

A modified example of a construction of characteristic variable filter 22 in the pulse wave detection device described in the first embodiment will now be described in the following. The other constructions are similar to those described in the first embodiment.

Figure 11:
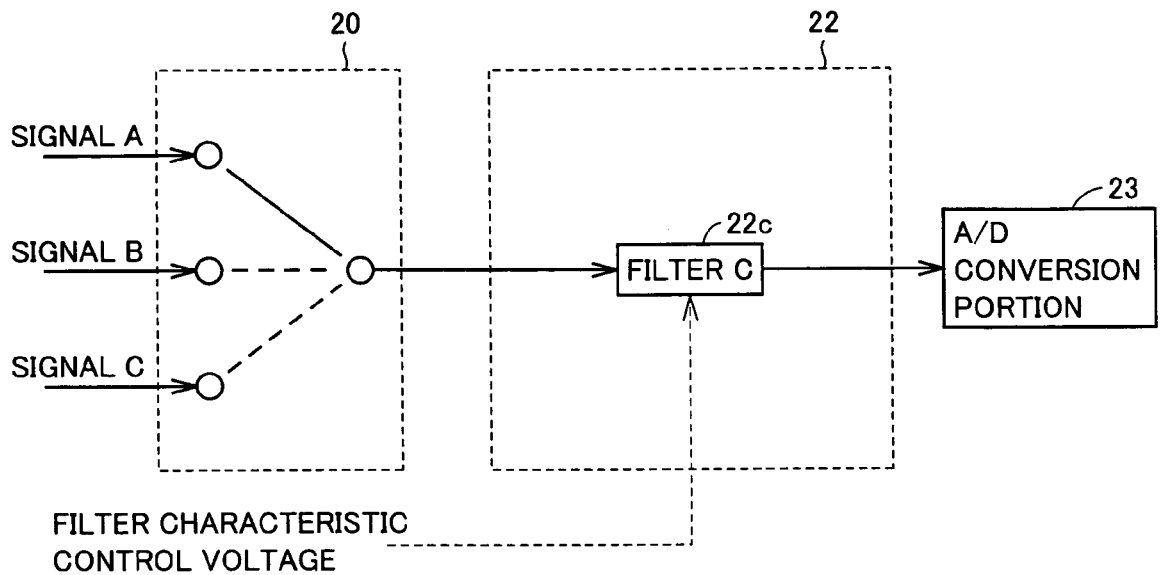
FIG. 11 shows a modified example of the characteristic variable filter in the first embodiment of the present invention.

FIG. 11 shows the modified example of the construction of characteristic variable filter 22 in the first embodiment.

Referring to FIG. 11, in the modified example, a filter C 22c having a variable frequency characteristic is used in place of a plurality of analog filters having different frequency characteristics. Filter C 22c is formed with a variable capacitance diode. CPU 11 applies a voltage to filter C 22c from a control circuit which is not shown. With this, a cutoff frequency in filter C 22c can be varied.

In this modified example, in the step indicated with S107 in FIG. 5, CPU 11 applies a control voltage so that a cutoff frequency $fc_C$ in filter C 22c becomes a value of at least switching frequency fx. In this situation, it is assumed that cutoff frequency $fc_C$ is set to, for example, 250 kHz.

In addition, in the step indicated with S121 in FIG. 5, CPU 11 applies a control voltage to vary cutoff frequency $fc_C$ to, for example, 100 Hz so that filter C 22c functions as an antialiasing filter.

With the construction as the modified example, size reduction can be attained because provision of a plurality of analog filters having different frequency characteristics is not required.

It is to be noted that, though the variable capacitance diode is used in the modified example to vary a cutoff frequency component, an element is not limited to this as long as it can vary the cutoff frequency component.

According to the first embodiment and the modified example thereof of the present invention as described above, since multiplexer 20 and characteristic variable filter 22 are dynamically controlled, a channel can be selected appropriately and an aliasing noise can be eliminated. Therefore, pulse wave data with high accuracy can be obtained.

With this, the pulse wave data for one pulse can be utilized for various analyses. As an example, a variation in movement of a heart after an administration of a medicine to a subject can be detected in real time on a pulse-by-pulse basis.

In addition, a time required for pulse wave measurement can be decreased since a pulse wave analysis for each pulse is enabled.

It is to be noted that, though one sensor element 28 is adopted as the optimum channel in this embodiment, two or more sensor elements may be adopted provided that a number thereof is smaller than a total number of sensor elements 28.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulse wave detection device, comprising:
   a sensor array having a plurality of pressure sensors arranged on a measurement surface;
   a pressurization portion for pressing said sensor array laid across an artery of a living body;
   a sensor signal selection portion for selecting a pressure signal among pressure signals from said plurality of pressure sensors; and
   a filter portion having a cutoff frequency variable corresponding to an instruction; wherein
   said filter portion cuts off a signal component having a frequency of at least a prescribed value included in the pressure signal selected by said sensor signal selection portion corresponding to said cutoff frequency; said pulse wave detection device further comprising:
   an analog/digital conversion portion for converting an analog signal passed through and output from said filter portion into a digital signal;
   a pressure sensor specification portion for specifying a pressure sensor for pulse wave detection among said plurality of pressure sensors;
   a pulse wave detection portion for detecting a pulse wave from said artery based on the digital signal corresponding to the pressure signal from the pressure sensor specified by said pressure sensor specification portion; and
   a filter control portion for providing the instruction to vary said cutoff frequency in said filter portion; wherein
   said filter control portion switches said cutoff frequency from a first value in a first situation wherein a plurality of pressure signals respectively obtained from said plurality of pressure sensors are successively switched and output by said sensor signal selection portion to specify said pressure sensor for pulse wave detection, to a second value in a second situation wherein the pulse wave is detected by said pulse wave detection portion.

2. The pulse wave detection device according to claim 1, wherein
   said first value corresponds to a value of at least a switching frequency of said plurality of pressure signals in said first situation, and said second value corresponds to a value enabling to eliminate an aliasing noise in said second situation.

3. The pulse wave detection device according to claim 2, wherein
   the value enabling to eliminate said aliasing noise is at most half a value of a sampling frequency for one pressure signal of said plurality of pressure signals.

4. The pulse wave detection device according to claim 1, wherein
   said filter portion includes
   a plurality of filters having different frequency characteristics, and
   an output selection portion for selecting one output among outputs from said plurality of filters.

5. The pulse wave detection device according to claim 4, wherein
   said plurality of filters include
   a first filter having said cutoff frequency of a value of at least a switching frequency of said plurality of pressure signals and
   a second filter having said cutoff frequency of a value enabling to eliminate an aliasing noise, and
   said filter control portion makes said output selection portion select an output from said first filter in said first situation and an output from said second filter in said second situation.

6. The pulse wave detection device according to claim 1, wherein
   said filter portion includes a variable capacitance element having a capacitance varying corresponding to a voltage applied from the outside, and
   said filter control portion varies the value of said cutoff frequency by applying a voltage to said variable capacitance element.

7. The pulse wave detection device according to claim 1, further comprising
   a sensor signal selection control portion for controlling an operation of said sensor signal selection portion, wherein
   said sensor signal selection control portion switches between a first operation to successively switch and output the plurality of pressure signals respectively obtained from said plurality of pressure sensors and a second operation to select and output the pressure signal from said specified pressure sensor.

8. The pulse wave detection device according to claim 1, wherein
   adjustment of a pressurization level of said pressurization portion and selection of said pressure sensor for pulse wave detection are performed concurrently.

9. A method of detecting a pulse wave, comprising the steps of:
   selecting a pressure signal with successively switching a plurality of pressure signals respectively obtained from a plurality of pressure sensors arranged on a measurement surface;
   low-pass-filtering said selected pressure signal with a first cutoff frequency;
   specifying a pressure sensor for pulse wave detection among said plurality of pressure sensors based on said low-pass-filtered pressure signal;
   selecting a pressure signal from said pressure sensor specified among said plurality of pressure signals as a pulse wave signal for pulse wave detection;
   low-pass-filtering said selected pulse wave signal with a second cutoff frequency lower than said first cutoff frequency; and
   detecting a pulse wave from said low-pass-filtered pulse wave signal.

10. The method of detecting a pulse wave according to claim 9, wherein
    said first cutoff frequency has a value of at least a switching frequency of said plurality of pressure signals, and said second cutoff frequency has a value of at most half a value of a sampling frequency for one pressure signal of said plurality of pressure signals.

* * * * *